United States Patent [19]

Wilson et al.

[11] Patent Number: 4,816,563

[45] Date of Patent: Mar. 28, 1989

[54] PROCESS FOR OBTAINING TRANSFER FACTOR FROM COLOSTRUM, TRANSFER FACTOR SO OBTAINED AND USE THEREOF

[75] Inventors: Gregory B. Wilson; Gary V. Paddock, both of Mount Pleasant, S.C.

[73] Assignee: Amtron, Inc., Charleston, S.C.

[21] Appl. No.: 670,596

[22] Filed: Nov. 15, 1984

Related U.S. Application Data

[63] Continuation-in-part of Ser. No. 554,921, Nov. 25, 1983, abandoned.

[51] Int. Cl.$^4$ .................. A61K 39/00; A61K 39/02; A61K 39/12; C07H 15/12
[52] U.S. Cl. .................... 530/344; 530/300; 536/22; 536/23; 536/24; 536/27; 514/2; 514/7; 514/8; 424/88; 424/89; 424/92; 424/105; 435/68
[58] Field of Search .............. 424/95, 105, 88, 89, 424/92, 93; 514/2, 7, 8; 530/350, 300, 832, 833, 344, 300; 536/22, 23, 24, 27

[56] References Cited

PUBLICATIONS

France et al *Clin Res*, vol. 28 863 A 1981 "Transfer Factor from Human Colostrum and Breast Milk Lymphocytes".
Ruben et al *Clin Res* vol. 27(4) 1979 698 A "Cell Medicated immunity to influenza A virus and influenza B virus in human colostrum and milk".
Meggs et al *Am J. Obstet Gynecol* vol. 133(6) 1979, pp. 703-707 "In-vitro Stimulation of human colostral lymphocytes by cytomegalovirus".
Parmely et al *J. Dairy Science* vol. 60(4) 1977 pp. 655-665 "Colostral cell medicated immunity and the concept of a common secretory immune system".
Schlesinger et al *Lancet* vol. 2 1977 pp. 529-532 "Evidence for transmission of lymphocytes response to tuberculin by breast feeding".
Wilson et al *Immunobiology* of *Transfer Factor* 1983 Kirkpatrick, Colt et al editors p. 331.
Wilson et al. *Immunology Today* vol. 4, p. 157.

*Primary Examiner*—Thomas G. Wiseman
*Assistant Examiner*—Robin L. Teskin
*Attorney, Agent, or Firm*—John P. White; John J. Santalone

[57] ABSTRACT

Antigen specific excreted transfer factor may be obtained by collecting material, e.g. colostrum or milk, secreted by the mammary gland of a suitable lactating mammal, e.g. a cow having immunity to the antigen under suitable conditions such that materials which interfere with transfer factor efficacy are removed so as to obtain transfer factor. Colostrum or milk so collected may be used directly, typically after sterilization, or may be treated to further concentrate and/or purify transfer factor. Treatment to yield colostral whey containing transfer factor is presently the preferred method for obtaining transfer factor for use in conferring immunity against diseases associated with antigens for which the transfer factor is specific. Cell-associated transfer factor specific for an antigen may also be obtained by incubation release from, or lysis of, cells obtained from the collected material. An alternative method for obtaining transfer factor is to recover it from the mammary tissue of a suitable lactating mammal. The transfer factor may be used in edible compositions and in pharmaceutical or veterinary compositions and in methods for conferring immunity in a human or lower animal to a disease associated with the antigen. The transfer factor may then be used to prevent or treat the disease.

28 Claims, No Drawings

PROCESS FOR OBTAINING TRANSFER FACTOR FROM COLOSTRUM, TRANSFER FACTOR SO OBTAINED AND USE THEREOF

BACKGROUND OF THE INVENTION

This application is a cont,inuation-in-part of U.S. Ser. No. 554,921 now abandoned filed Nov. 25, 1983, the contents of which are hereby incorporated by reference into the present application.

During the first few days of lactation, the mammary gland secretes a fluid called colostrum which is quite different from normal milk. Both colostrum and milk contain antibodies of the humoral immune system and cells known to function in the cellular immune system including T cells, B cells and macrophages. (Watson, D. L., 1980, Aust. J. Biol. Sci. 33:403; Outteridge, P. M. and Lee, C. S., 1981, Adv. Exp. Med. & Biol. 137:513). The ratios and quantities of the various antibodies and cell types vary between milk and colostrum for a given species and between species (Watson, 1980; Outteridge and Lee, 1981). While the antibodies produced in colostrum are known to be able to survive the infant digestive tract and confer immunity at least in some species (e.g., bovine), the various cell types found probably are less hardy and, if they do survive, are believed to provide immunity only to localized regions (Watson, 1980; Outteridge and Lee, 1981). Although Watson indicated that "the possibility remains that cell-mediated immune phenomena might be transferred from mother to young from the passage of soluble factors produced by lymphocytes, such as transfer factor," neither Watson nor any one else has reported either the transfer of cellular immunity using soluble products from colostrum or colostral cells, or the presence of transfer factor in colostrum or colosural cells. On the contrary, recent papers indicate that colostrum lacks optimal numbers of natural killer cells, Kohl, S., et al., 1978, J. Clin. Lab. Immunol. 1:221–224, Human Colostral Cytotoxicity, and that colostrum or milk block the ability of broad spectrum stimulants to induce cell mediated immunity, may block the killing of foreign cells by normal peripheral blood lymphocytes or neutrophils, and actually suppress cell mediated immunity when given to animals or mixed with cells in vitro Ogra, S. S. and Ogra, P. I., 1978, J. Pediatr. 92:550–555; Crago, S. S., et al., 1981, Clin. Exp. Immunol. 45:386–392. Moreover, since transfer factor was heretofore reported to be found only in or on lymphocytes, i.e. not in a cell-free state in large quantities, the presence of such transfer factor in elevated amounts in colostrum is totally unexpected and provides a readily available, inexpensive source for this otherwise rare and expensive material. Finally, the presence of T lymphocyte cells in colostrum does not mean that transfer factor will be present. It is well-known that serum and blood which contain lymphocytes do not contain transfer factor unless the lymphocytes are stimulated with antigen. Furthermore, all of the literature concerning transfer factor teaches that transfer factor should be a product of helper or inducer T cells. In order for colostrum to be of value as a source of transfer factor, helper T cells ought to markedly outnumber suppressor T cells (as in peripheral blood) since suppressor cells are a source of products believed to negate the effects or action of transfer factor. The relative ratios of helper and suppressor T lymphocytes have been reported to be lower in colostrum than in peripheral blood, leading to the conclusion that the physiologic role of T lymphocytes in colostrum is "not yet clear and cannot be predicted." Richie et al., 1982, J. Immunol. 129:1116–1119.

It is known that transfer factor can stimulate or transfer cell-mediated immunity against certain diseases in man and other animals and that this transfer can be made between species (Fudenberg, H. H., Wilson, G. B., Goust, J. M., Nekam, K., and Smith, C. L., 1980, in *Thymus, Thymic Hormones and T Lymphocytes*. Aiuti, F. and Wigzell, H., eds., London, Academic Press, p. 391; Wilson, G. B. and Fudenberg, H. H., 1983, Immunology Today 4:157; Klesius, P. H., Fudenberg, H. H., Smith, C. L., 1980, Comp. Immunol. Microbiol. Infec. Dis. 3:247). It is also known that transfer factor can be obtained from tissues such as blood serum leukocytes or lymph node lymphocytes but these sources require time consuming and expensive leukophoresis or animal sacrifice and laborious extraction procedures (Wilson and Fudenberg, 1983; Klesius et al., 1980; Klesius, P. H. and Kristensen, F., 1977, Clin. Immunol. Immunopathol. 7:240; Wilson, G. B. and Fudenberg, H. H., 1981, Lymphokines 4:107). The yield of transfer factor is relatively small for the effrrt and quantity of tissue involved. It is further known that transfer factor inside immune cells from various tissues can be obtained via freeze-thaw lysis, and that it can be obtained by incubating these cells with or without antigens or organisms to release TF into the media (Wilson, G. B., Fundenberg, H. H., Paddock, G. V., Tsang, K. Y., Williams, A. M. and Floyd, E., 1983, in *Immunobiology of Transfer Factor*, Kirkpatrick, C. H., Burger, D. R. and Lawrence, H. S. eds., New York, Academic Press, p. 331). It is also known that transfer factor is specific for a given antigen to which the source animal has received prior exposure or immunization (Wilson and Fudenberg, 1983; Wilson and Fudenberg, 1981) and that transfer factor of a given antigen specificity can be obtained when leukocytes are incubated with that antigen or organism from which that antigen is derived (Wilson et al., 1983). Finally, it is known that transfer factor for a given antigen can be induced by serial transfer of transfer factor for that antigen from an immune subject to another subject (Kirkpatrick, C. H. and Smith, T. K., 1976, Cell. Immunol. 27:323).

SUMMARY OF THE INVENTION

This invention provides an inexpensive process for obtaining transfer factor (TF) in virtually unlimited quantities from readily available sources. Specifically, excreted TF specific for an antigen may be obtained by collecting material secreted by the mammary gland of a suitable lactating animal, e.g. colostrum or milk from a cow having immunity to the antigen, under suitable conditions such that materials which interfere with TF efficacy are removed so as to thereby obtain TF. Preferably colostrum is employed as the TF source and is treated to separate cells, cells debris, casein, immunoglobulins and other unwanted materials from colostral whey containing the TF.

If desired the transfer factor may be further concentrated or purified or both. Separation, concentration and purification methods which may be used include one or more of the fllowing: centrifugation, extraction, precipitation, ultrafiltration, dialysis, chromatography and lyophilization. Alternatively, cell associated transfer factor may be obtained from the separated colostral cells by incubation release or by cell disruption. In addition to colostrum and milk, transfer factor may be obtained from the mammary tissue of a suitable lactating mammal.

The transfer factor so prepared may be incorporated into edible compositions or into pharmaceutical or veterinary compositions for the prevention or treatment of a disease associated with an antigen for which the TF is specific. The TF may be employed to confer immunity against disease asociated with the antigen for which it is specific, e.g. *Mycobacterium bovis, Coccidioides immitis,* herpes simplex virus, human mump virus, bovine rhinotracheitis virus; bovine parainfluenza virus, Newcastle's disease virus, Marek's disease virus, infectious bronchitis virus, laryngotracheitis virus, a protozoan or a cancer-related antigen.

DETAILED DESCRIPTION OF THE INVENTION

The description which follows involves at least three forms of transfer factor (TF). One form, excreted transfer factor (TFe), is released from TF-containing cells and may be collected from extra-cellular fluid. A second form, pre-excreted TF (TFpre) occurs within the cell or on the cell surface and is believed to be released, following structural modification, as TFe. The third form of TF, internal TF (TFi), is also found within te cell or on the cell surface, and is believed to differ in chemical structure from both TFe and TFpre. TFpre and TFi are also referred to herein as cell-associated TF. The three forms of TF are described in greater detail below.

Excreted transfer factor (TFe) specific for an antigen may be obtained by collecting material secreted by the mammary gland of a suitable lactating mammal under suitable conditions such that materials which interfere with transfer factor efficacy, i.e. its activity in conferring cell mediated immunity, are removed so as to thereby obtain transfer factor. Colostrum in particular is a rich source of transfer factor. While TFe may also be obtained fro.m milk, the concentration of TFe is more variable in milk than in colostrum. Colostrum is therefore the presently preferred material for obtaining TFe. Use of colostral or milk whey thus provides a simple method for obtaining large quantities of TFe inexpensively. Alternatively, mammary tissue may be used as a source of transfer factor.

A suitable lactating mammal for use in this invention is a mammal, e.g. a human, cow or goat, which has immunity to an antigen. Such a mammal may be identified by screening to determine the presence of such immunity or the mammal may be rendered immune by injecting antigen or transfer factor specific for an antigen into the mammal or otherwise exposing it to antigen before it commences lactation. The transfer factor obtained from the mammal is specific for a given antigen.

The suitable mammal may be appropriately immunized by conventional methods known in the art, e.g. intraperitoneal, subcutaneous or intramuscular injection of an appropriate antigen. A sufficient period of time, generally at least about one to two weeks, must be allotted after immunizing the mammal and before collecting the material, e.g. colostrum or milk, for the mammal to respond to the immunogen (antigen). Typically, where the suitable mammal is a cow the cow is immunized by injection of the immunogen between the fifth and seventh month of gestation. In one embodiment a primary injection is administered to the cow between six and one-half and seven months into the gestation period, followed by a secondary (booster) injection three to four weeks later, thus leaving one to one and one-half months before calving and collection of post-parturition parturition colostrum, for example. Alternatively, the primary injection may be administered during the fifth month of gestation, followed by a secondary injection three to four weeks later and a subsequent tertiary injection, again leaving a period of one to one and one-half months for the cow to respond to the immunogen before calving. In cases where the animal has been maintained on a routine schedule of annual booster immunizations, TF-containing material generally may be collected throughout the year, after the second booster injection.

Commercial veterinary vaccines where available are suitable for immunizing the mammal using a conventional amount and protocol as for routine vaccination. Thus, a cow may be suitably immunized with commercially available bovine rhinotracheitis virus vaccine (Salsbury Laboratories, Inc., Charles City, Iowa) or bovine parainfluenza virus (Salsbury Laboratories) using the same methods and amounts as for routine vaccination. Immunization with *Mycobacterium bovis* is suitably effected for example, by the method of Klesius, P. H. and Fudenberg, H. H., 1977, Clin. Immunol. and Immunopathol. 8:238–246. Immunization of a cow against pathogens such as Newcastle's disease virus, Marek's disease virus, infectious bronchitis virus and laryngotracheitis virus may be effected by injecting the cow with one to three vials of the poultry vaccine as obtained from the supplier (Salsbury Laboratories). Each vial contains about 1,000 chicken doses of vaccine. Alternatively, vaccines prepared by methods known in the art may be similarly administered to the suitable mammal. Thus a cow may be suitably immunized by one to three injections of 3.5–7 mg/injection of spherulin, a preparation of formalin killed spherules of washed in saline and stored in physiological saline at a concentration of 7 mg dried killed spherules/cc of physiological saline, for example. Similarly, the cow may be immunized by injection with $10^7$–$10^8$ PSU of viable attenuated herpes simplex virus. Those of ordinary skill in the art will appreciate that the precise amount of antigenic materials to be injected will depend on the size and responsiveness of the cow or other animal to be immunized.

Transfer factor potency of the material collected or fractions thereof may be determined using an assay previously described (Wilson, G. B., Metcalf, J. F. and Fudenberg, H. H., 1982, Clin. Immunol. Immunopathol. 23:478; also co-pending U.S. patent application Ser. No. 650,498, now abandoned U.S. Pat. No. 4,610,878 filed June 16, 1983 names of G. B. Wilson and H. H. Fudenberg entitled "Use of in vitro Assay Techniques To Measure Parameters Related To Clinical Applications of Transfer Factor Therapy"). The TF concentration of the collected material (in potency units, PU, as measured by the aforementioned assay) depends upon how well the suitable mammal responds to the immunization and the time at which the material is collected relative to parturition, among other factors.

Colostrum or milk obtained from a suitably lactating female mammal may be used directly as a composition for treatment or the like. Alternatively, one may treat the collected material, e.g. by ultrafiltration or dialysis, to recover the transfer factor therefrom.

When leukocytes are incubated that do not already release TF of a given antigen specificity, they can be made to do so by incubating them with that antigen, i.e. to produce incubation release TFe (IR-TF). Wilson, G. B., Fudenberg, H. H., Paddock, G. V., Tsang, K. Y., Williams, A. M. and Floyd, E., 1983, in *Immunobiology of Transfer Factor.* Kirkpatrick, C. H., Burger, D. R. and Lawrence, H. S. eds., New York, Academic Press, pp. 331-336. In one embodiment colostrum is collected and treated so as to substantially remove cells, cell debris, casein and fat. The removed cells may then be contacted under suitable conditions with the antigen so that the cells release TFe using the protocols of Wilson et al., 1983. The TFe may then be concentrated or purified and the concentrated or purified TFe sterilized. Sterilization in this and other embodiments may be suitably effected with a commercially available filter sterilization unit, e.g. a $0.2\mu$ Nalgene unit.

Suitably the treatment to substantially remove cells, cell debris, casein and fat comprises low speed centrifugation (e.g. 100-12,000 g) for a period of time, e.g. 5 minutes to 1 hour, followed by high speed centrifugation (e.g. 10,000-100,000 g) for another period of time, e.g. 10 minutes to 1 hour. Low speed centrifugation in this and other embodiments encompasses not only traditional centrifugation but also processing in a conventional cream separator.

In one embodiment pre- and post-parturition colostrum (or milk) is collected and centrifuged at low speed, approximately 38 g (100 to 2000 g), for 15 min at about 4°-37° C. These lower speeds are preferred where collection of cells for subsequent use is desired. The fat is skimmed from the surface and the remaining supernatant is decanted from the pelleted cells. The pelleted cells are saved for preparation of cellular dialyzable leukocyte extract (DLE), i.e. cell associated TF as described below or incubation released (IR) TF as previously described. The defatted supernatant is then centrifuged at high speed, approximately 25,000 g (10,000 to 110,000 g) for 30-60 min at about 4°-37° C. Lower g forces likely may also be employed but the time required would be longer and the product might be less pure. Centrifugation may also be conducted solely at higher g forces, although such treatment may preclude the survival of viable cells or the recovery of cells without gross contamination with fat or casein or both. Any remaining fat is skimmed from the top of the material and the remaining supernatant (colostral whey) is decanted from the casein and cell debris. Alternatively, casein may be precipitated by addition of $CaCl_2$ and rennin to, or by acidification (pH4-5) of, the low speed supernatant and the precipitate removed by filtration or centrifugation using standard procedures (Schultze, H. E. and Heremans, J. F., 1966, *Molecular Biology of Human Proteins,* Amsterdam, Elsevier Biomedical Press, Vol. 1, pp. 832-847; U.S. Pat. No. 4,051,23 issued Sept. 27, 1977. Alternatively, the casein precipitation may be done using sequential precipitations first by $CaCl_2$ and rennin followed by dialysis of the whey and a second precipitation of the casein from the whey by acidification. The resulting colostral whey transfer factor may be sterilized via filtration or other techniques such as passage through a water sterilizer (UV) and its potency assayed using the aforementioned techniques (Wilson et al., 1982). The colostral whey transfer factor may be directly suitable for packaging and use or may be further treated. Administration may be orally, topically or by injection.

Alternatively, the treatment may comprise low speed centrifugation of the colostrum, as previously disclosed, followed by addition of a suitable amount of an agent which also substantially precipitates immunoglobulins. In this embodiment the pH of colostral whey may be adjusted to approximately pH 6.0 by use of 0.1 volume of 3M sodium acetate and the colostral whey transfer factor subsequently precipitated using ethanol precipitation at 0°-4° C. or -20° C. (up to two volumes ethanol) and -20° C. (up to 4 volumes ethanol). The interface does not need to be preserved before mixing as previously thought (Klesius, P. H. and Fudenberg, H. H., 1977, Clin. Immunol. Immunopathol. 8:238; U.S. Pat. No. 4,180,627 issued Dec. 25, 1979 to Klesius, P. H. and Fudenberg, H. H.). Instead the aqueous and ethanol phases may be immediately mixed. After chilling for from 1 hour to overnight, the transfer factor precipitate may be collected by centrifuging at approximately 12,000 g (10,000 to 20,000 g). Fractionation of colostral whey transfer factor may be enhanced by sequentially adding 0.5 volumes of ethanol to supernatants in steps followed by chilling and centrifuging as above. In summary, purification by ethanol precipitation may be accomplished and a variety of parameters may be varied [e.g. ionic strength, pH, temperature, ratio of ethanol to water added at each step, concentration of nucleic acid and protein (one may even desire to add transfer RNA as an inert carrier substance for precipitation of transfer factor in dilute solutions)]. These parameters have been varied and it has been found that for a given ethanol to water ratio, the transfer factor may be moved from precipitate to supernatant depending on the conditions used for a given purification. Sequential fractionation using other water miscible organic solvents such as isopropanol, t-butanol or acetone may also be used to remove unwanted contaminants from transfer factor. Reagents known to those of ordinary skill in the art for precipitating peptides and nucleic acids, e.g. alcohohols, ketones and polyethylene glycol, likely may also be used to precipitate transfer factor or to unwanted contaminants from transfer factor.

In other embodiments the material collected e.g. colostrum, is treated with low speed centrifugation as disclosed above, followed by ultrafiltration or dialysis. In these embodiments the transfer factor may be separated from larger molecules using conventional dialysis membranes or filters with known molecular weight cut-offs, e.g. a 20,000 molecular weight cut-off. The filtration or dialysis may be carried out after precipitation of contaminants where the organic solvent, e.g. isopropanol, is compatible with the filter or membranes. The transfer factor may also be separated from smaller molecules by using conventional dialysis membranes or filters with known molecular weight cut-offs, e.g. a 1,000 molecular weight cut-off.

Transfer factor obtained by any of the above-mentioned methods may then be concentrated or purified or both, e.g. by ultrafiltration or lyophilization or both, and the concentrated or purified transfer factor sterilized. Typically, sterilization is effected using known methods either directly, or after further treatment to concentrate and/or purify transfer factor.

There are a number of additional steps which can be employed to improve product quality with regard to concentration, potency, stability and removal of contaminants. For example:

1. The colostral whey transfer factor may be lyophilyzed and stored dry for later use and/or reconstituted in sterile pyrogen-free water, physiologic saline or any other fluid suitable for injection or oral administration;

2. The colostral whey transfer factor may be extracted sequentially with phenol and ether (to remove residual phenol) at room temperature. Other solvents known to denature and remove protein or to exclude nucleic acids, e.g. $CHCl_3$ or butanol, may also be used;

3. The colostral whey transfer factor may be further purified by chromatographic, e.g., cellulose, boronate, reverse phase, Sephadex, etc.; electrophoretic, e.g., acrylamide gels; or immunologic, e.g. antigen binding, techniques

[Paddock, G. V., Wilson, G. B., Williams, A. M. and Fudenberg, H. H., 1983, in *Immunobioloov and Transfer Factor* (Kirkpatrick, C. H., Burger, D. R. and Lawrence H. S., eds.), New York, Academic Press, p. 51; Wilson et al., 1983, p. 31].

As previously indicated, milk may be used in place of colostrum in the various embodiments of this invention although colostrum is preferred as the transfer factor source. Where milk is used in place of colostrum, transfer factor may be obtained in the same fashion. Thus, the milk may be treated by the aforementioned methods so as to substantially remove cells, cell debris, casein and fat. Similarly, cells removed from the milk may also be contacted under suitable conditions with the antigen so that the cells release transfer factor. Furthermore the cells may be removed and the transfer factor concentrated or purified and then sterilized. Similarly the cells may be lysed to obtain cell-associated TF.

The antigens to which specific transfer factor may be obtained by this invention are numerous and varied. Suitably the antigen is or is derived from a microorganism such as a bacterium, fungus, protozoan, Rickettsia, mycoplasma, or virus associated with a disease of humans, lower mammals or other animals such as fowl, e.g. chickens.

Diseases of fowl include fowlpox, avian encephalomyelitis, infectious bursal disease, viral arthritis, mycoplasma gallisepticum, mycoplasma synoviae, Newcastle's disease, Marek's disease, infectious bronchitis, and laryngotracheitis.

Mammalian diseases include foot and mouth disease; rinderpest; bovine viral diarrhea; transmissible gastroenteritis; African swine fever; pseudorabies; swine dysentery; rabies; equine infectious anemia, influenza, viral arthritis and viral rhinopneumonitis; swine influenza; micoplasma hypopneumoniae; feline infectious anemia; canine distemper, infectious hepatitis and herpes virus; parvovirus; *coccidiosis sp.; lungworm sp.; asceris sp.;* salmonella; erysipelothrix; *Escherichia coli;* brucellosis; leptospirosis; anthrax; trypanosomiases; babeiosis; anaplasmosis; *pasteurella sp.;* ulcerative dermatosis; and contagious ecthyma; bovine rhinotracheitis; bovine parainfluenza; and *Mycobacterium bovis*.

Human diseases include fungal diseases, e.g. *Mucocutaneous candidiasis,* vaginal candidiasis, histoplasmosis and coccidioidomycosis; mycobacterial diseases, e.g. tuberculosis, leprosy, mycobacterium fortitum and mycobacterium intracellulariae; protozoal diseases, e.g. *Plasmodium vivax, Trypanosoma gambiense, Trypanosoma prhodesiense, Pneumocystis carinii, Leishmania tropica* and *Leishmania donovani;* neuroviral immunological disorders, e.g. multiple sclerosis and Guillain-Barre syndrome; cancers, e.g. osteosarcoma, breast cancer, hypernephroma, nasopharyngeal carcinoma, melanoma, alveolar carcinoma, renal carcinoma, epidermodysplasia verruciformis and other cancers, especially those thought to have a viral epidemiology; autoimmune diseases, e.g. chronic discoid lupus erythematosus and Behcett's syndrome; nemathelminthes, e.g. *Toxocara canis* and *Wuchereria bancrofti;* platyhelminthes, e.g. *Taenia solium* and *Echinococcus granulosus;* platyhelminthes flukes, e.g. Schistosomia mansonia; viruses, e.g. Hepatitis B, *Eczema vacciniatum,* pox viruses, herpes viruses, adenoviruses, papova viruses, picorna viruses, rhinoviruses, Toga viruses, Bunya viruses, Reo viruses, Ortho- and paramyxo viruses including mumps, Rhabdo viruses, Retroviruses, Arena viruses, Corona viruses and miscellaneous viruses such as chronic infectious neuropathic agents and other diseases such as rhematoid arthritis; asthma; infections of bacteria, chlamydiae, mycoplasmas and rickettsiae; or diseases associated with a prion.

Another method of this invention permits obtaining cell-associated transfer factor specific for an antigen. This method involves collecting material secreted by the mammary gland of a suitable lactating animal as described above, recovering whole cells from the material collected and treating the whole cells so recovered under suitable conditions such that materials which interfere with transfer factor efficacy are removed so as to thereby obtain transfer factor.

In one embodiment the treatment comprises disrupting the cells to release transfer factor by a method such as freeze-thaw lysis or sonication, and recovering transfer factor from the disrupted cells. The cell disruption method may be applied repeatedly to ensure thorough disruption. The transfer factor released from the disrupted cells may be recovered by the methods previously disclosed, e.g. centrifugation, fractional precipitation, ultrafiltration, dialysis (ie. for DLE), etc. The transfer factor so obtained may then be concentrated or purified or both, again by previously disclosed methods, e.g. lyophilyzation, extraction, chromatography, etc., and the concentrated or purified transfer factor sterilized. By this method cell-associated transfer factor specific for numerous and varied antigens may be obtained. Cell-associated transfer factor specific for *M. bovis,* for example, may be obtained in this fashion. In one embodiment bovine-derived cell-associated transfer factor specific for *M. bovis* is obtained from material collected from a suitable lactating cow.

Thus, by the methods of this invention transfer factors specific for numerous and varied antigens may be obtained. For example, bovine-derived transfer factor specific for *Coccidioides immitis,* TFe specific for *C. immitis,* and bovine-derived TFe specific for *C. immitis* may also be obtained by this invention.as may TFe and bovine-derived TFe specific for herpes simplex virus. Similarly, transfer factor, including TFe, may be obtained which is specific for bovine rhinotracheitis virus, bovine parainfluenza virus, Newcastle's disease virus, Marek's disease virus. infectious bronchitis virus or laryngotracheitis virus. In embodiments using material collected from a suitable lactating cow, bovine-derived transfer factor, including TFe, with the above-mentioned specificities may be obtained. By using the purification methods described herein purified TF's of the above-mentioned specificities and forms may be readily obtained.

In summary TFe and cell-associated transfer factor may be obtained by the above-mentioned methods, including the incubation release method or cell disruption using colostral or milk cells. Because the TF sources of this invention are so rich in transfer factor, are atural sources and can be used to obtain homogeneous transfer factor or mixtures of transfer factor specific for a variety of diseases, the transfer factor may be used as a health food or food supplement or additive that would greatly increase immunity toward disease. One embodiment of this invention thus involves an edible composition comprising transfer factor obtained by one or more of the various methods of this invention and a suitable edible carrier.

Because the transfer factor can be obtained in high yield and in purified form, it may be used as a reagent or for making reagents of value in research or diagnostics in pharmaceutical or veterinary formulations. The transfer factor can be incorporated into pharmaceutical or veterinary compositions and employed to confer immunity in man and other animals (e.g., livestock, poultry or pets, e.g. dogs or cats) against disease associated with the antigen for which the TF is specific. It should be understood by those of ordinary skill in the art that a composition containing transfer factor capable of conferring such immunity in a subject may be used as a therapeutic or prophylactic agent against the disease associated with the antigen for which the transfer factor is specific. Such a pharmaceutical or veterinary composition comprises an effective immunity conferring dose of transfer factor obtained by one or more of the various methods of this invention and a suitable pharmaceutical or veterinary carrier of which many are known in the art. This invention encompasses veterinary compositions for conferring immunity in a cow to *M. bovis*, herpes simplex virus or bovine parainfluenza virus, for example, and for conferring immunity in a fowl, e.g. a chicken, to Newcastle's disease virus, Marek's disease, infectious bronchitis or laryngotracheitis, for example. The invention further comprises pharmaceutical compositions for conferring immunity in a human subject to disease-causing agents such as *Coccidioides immitis*, herpes simplex virus and human mumps virus. Such compositions comprise an effective immunity-conferring dose of transfer factor specific for the antigen with which the disease is associated and a suitable veterinary or pharmaceutical carrier. The suitable carrier may be selected from numerous known carriers which have been used in other veterinary or pharmaceutical compositions. The transfer factor potency of the material to be used in such compositions may be determined using the leukocyte migration inhibition (LMI) assay described in Wilson, G. B., Metcalf, J. F. and Fudenberg, H. H., 1982, Clin. Immunol. Immunopathol. 23:478 and Wilson, G. B. and Fudenberg, H. H., 1981, Lymphokines 4:107. By method the number of standard potency units (PU) of transfer factor in a sample may be determined. An effective immunity conferring dose of transfer factor contains about 1–4,000 PU/kg of body weight of the animal or human subject, preferably about 10–400 PU/kg of body weight. It should be understood by those skilled in the art that within the indicated dosage ranges a relatively higher dose would be required for clinical efficacy, i.e. the treatment or prevention of disease associated with the antigen to which the TF is specific, in a subject with higher antigen load (e.g., in a subject suffering a more extensive invasion by the microorganism or a larger tumor mass) or in a subject in relatively poor overall health. A relatively lower dose within the indicated dosage ranges may suffice as a prophylactic against infection by the antigen associated with the disease in a subject in generally good health.

The invention further encompasses a method of conferring immunity in a human or lower animal which comprises administering to the human or lower animal an effective immunity-conferring dose of transfer factor obtained by a method of this invention. Suitably the transfer factor may be administered orally, topically or by injection, and may be administered repeatedly. In one embodiment immunity to *M. bovis* may be conferred in a cow by administering to the cow an effective immunity conferring dose of cell-associated transfer factor specific for *M. bovis*.

Similarly, immunity to herpes simplex virus, bovine rhinotracheitis virus or bovine parainfluenza virus may be conferred in a cow for example, by administering to the cow an effective immunity conferring dose of TFe specific for herpes simplex virus, transfer factor specific for bovine rhinotracheitis or transfer factor specific for bovine parainfluenza virus, respectively. Immunity to Newcastle's disease virus, Marek's disease virus, infectious bronchitis virus or laryngotracheitis virus may be conferred in a chicken, for example, by administering to the chicken an effective immunity conferring dose of transfer factor specific for the respective viral antigen. Furthermore, immunity to *Coccidioides immitis*, herpes simplex virus or human mumps virus, for example, may be conferred in a human subject by administering to the subject an effective immunity conferring dose of bovine derived transfer factor specific for *C. immitis*. TFe specific for herpes simplex virus or bovine-derived transfer factor specific for human mumps virus, respectively.

Previous results from studying human, burro and bovine TF indicate that there are three different structural forms of TF for each antigen specificity as mentioned above. Two forms of the TF are intracellular or on the surface of immune lymphocytes, and one form of the TF is excreted (secreted) from immune cells incubated in vitro with or without antigen for defined periods (IR-TF) (Wilson and Fudenberg, 1983); Wilson et al., in Immunobiology of Transfer Factor, 1983, p. 331). For simplicity, these are referred to as TFi (TF intracellular, previously called TF7), TFpre (TF pre-excreted; previously called TF5 phosphorylated) and TFe (TF excreted, the TF which is released by immune lymphocytes (IR TF), also previously referred to as dephosphorylated TF5). To determine which forms of TF are present in colostral whey and which forms are present in colostral cells requires the examination of their physiochemical properties and structural features. TFs from colostral whey and from colostral cells were unequivocally present in the water phase after a two-step phenol-ether extraction and could be precipitated with ethanol. Thus, colostral whey and cellular TFs behaved similarly to IR TFs and DLE TFs of burro, human and bovine lymph node or peripheral blood leukocyte origin. No TF activity was lost through and including fractionation of TF containing material by cellulose TLC.

The TF in colostral whey has a structural relationship with that known for IR TF whereas colostral TF prepared via freeze-thawing of colostral cells contains at least one of the forms of TF expected for intracellular TF in significant amounts. The structural relationships (simple models that fit present data not to be considered detailed strucrures that would exclude other molecular structures which are as yet unknown) can be deduced from the data in Table I and the following simple block diagram models:

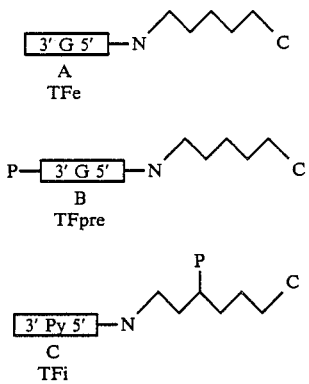

where

represents an oligoribonucleotide moiety in which the 3' (2') and 5' directions are indicated by 3' and 5', respectively, N represents an unknown small number of ribonucleotides in which TFe and TFpre have at least one internal purine likely to be guanosine (G) and TFi has at least one internal pyrimidine (Py). P represents an external phosphate sensitive to removal by phosphatase.

represents a peptide moiety in which the amino and carboxyl termini are represented by N and C, respectively. The bond joining the peptide and oligoribonucleotide is unknown and the above models are to be construed only as demonstration models not to exclude other molecular moieties that eventually may prove to be a part of TF structure.

Briefly, the various degradative enzymes (nucleases, ribonucleases, phosphatases, peptidases, and phosphodiesterases) were used to determine whether the TF activity could be destroyed by a given enzyme. Elimination of activity implies certain structural constraints on the TF molecule. The data supports basic ribonucleopeptide structures related to those previously deduced for TF in which there is a peptide (free carboxyl terminus; i.e., activity degraded by carboxypeptidase A) joined via its N-terminal end (i.e., activity not degraded by leucine amino peptidase) to an oligoribonucleotide (free 2', 3' end; i.e., activity degraded by snake venom phosphodiesterase) at its 5' end (i.e., activity not degraded by spleen phosphodiesterase).

There are three basic molecular structures with TF activity. Structure A has an internal guanosine (i.e., activity degraded by T1 RNase) and no phosphate at its 2', 3' end. Structure B has an internal purine likely to be guanosine and a phosphate at its 2', 3' end (i.e., activity degraded by snake venom phosphodiesterase only if a phosphate is removed by alkaline phosphatase). Structure C has an internal pyrimidine (activity degraded by RNaseA) and no phosphate at its 2', 3' end, but it does have a phosphate sensitive to removal by bacterial alkaline phosphatase, possibly attached to its peptide moiety. Structure A (Excreted TF; TFe) is found in the colostral whey and is the form of TF released by cells when they are incubated. Structures B (pre-excreted TF; TFpre) and C (internal TF; TFi) are found inside the cell or on the cell surface. All of the TF moieties represented by structures A, B, and C are able to confer antigen specific cell-mediated immunity. Structure B has a mobility on cellulose TLC (Methanol:HCl:H2O/70:20:10) roughly similar to that of guanosine whereas structures A and C have mobilities roughly similar to that of uridine 2' (3') monophosphate.

TABLE I

Enzyme Inactivation Studies on TF Activity

| | Enzyme | Activity A(TFe) | B(TFpre) | C(TFi) |
|---|---|---|---|---|
| 1. | P1 nuclease | − | − | − |
| 2. | T1 RNase | − | − | + |
| 3. | RNase A | + | + | − |
| 4. | Snake Venom phosphodiesterase (SV) | − | + | − |
| 5. | Bacterial alkaline phosphatase (BA)) | + | + | − |
| 6. | SV + BAP | − | − | − |
| 7. | Acid phosphatase (AP) | + | + | − |
| 8. | Spleen phosphodiesterase (SP) | + | + | + |
| 9. | AP + SP | + | + | − |
| 10. | Pronase | − | − | − |
| 11. | Carboxypeptidase A | − | − | − |
| 12. | Leucine amino peptidase | + | + | + |

Degradation of activity after treatment by enzymes indicated by (−) while no effect by enzyme on activity indicated by (+). The colostral whey TF used for A in these studies was purified via phenol and ether extraction, ethanol precipitation, and cellulose TLC. B and C are included from our previous studies of TFpre and TFi from other non-colostral sources for comparison.

EXAMPLES

Materials and Methods

In the examples below the following immunogen were used: Bovine rhinotracheitis virus, Marek's disease virus, Newcastle's disease virus, infectious bronchitis virus, laryngotracheitis virus and bovine parainfluenza virus, all of which may be obtained from Salsbury Laboratories, Inc., Charles City, Iowa; spherulin, as previously described, obtained from Dr. H. B. Levine, University of California, Naval Biosciences Laboratory, Naval Supply Center, Oakland, Calif.; and herpes simplex virus (viable attenuated HSV-1, strain 35, as previously described), obtained from Associate Professor R. A. Lausch, University of Alabama College of Medicine, Department of Microbiology and Immunobiology, Medical Science Building, Mobile, Ala. PPD-B, PPD-F, PPD-M and PPD-I may be obtained from the Statens Serum Institute, Copenhagen, Denmark (as may *Coccidioides immitis* antigen). Human mumps virus was obtained from Lilly, Berkeley, Calif. Commercial chickens were obtained from the S.P.D. Hatchery, South Carolina while SPAFA chickens were obtained from SPAFA, Inc. Organic solvents and chemicals, e.g. acetone, ethanol, ether, isopropanol and phenol, were all reagent grade or better, as may be obtained from Aldrich Chemical Co., Milwaukee, Wis.

The centrifuge used in the examples below is a Sorvall model RC2B centrifuge (E.I. duPont de Nemours & Co., Inc., Wilmington, Del.); the lyophilization is a Unitrap-II or model 10-147 MR-BA (Virtis Co., Gardiner, N.Y.); the filter sterilizing unit (0.2) is a Nalgene Filter Sterilizer (Nalge Co., Rochester, N.Y.) and the cream separator is an Electrocrem model 116036 (1984).

EXAMPLE 1

Excreted and Cell Associated Colostral Transfer Factor Specific for *Mycobacterium bovis*

A. Preparation of Colostral Excreted Transfer Factor

Postparturition colostrum was obtained from dairy cows either immune or nonresponsive to *Mycobacterium bovis* antigen (purified protein derivative from *M. bovis*; PPD-B). Each crude colostrum sample was centrifuged at 380 g at 4° C. for 30 min. to pellet the cells. The fat was skimmed from the surface of the supernatant and the remaining supernatant was decanted. The decanted supernatant was again centrifuged at high speed (25,000 g for 30 min at 4° C.) to remove casein and any remaining fat or solids. The decanted supernatant obtained after this high speed centrifugation is designated colostral whey. The colostral whey was subsequently fractionated using (a) dialysis, (b) phenol and ether extraction, (c) ethanol precipitation, (d) thin-layer chromatography, and (e) boronate chromatography following procedures developed by the inventors and previously employed to purify TF from burro DLE, human DLE, and human IR TF [Wilson, G. B., Paddock, G. V. and Fudenberg, H. H., 1982, Thymus 4:335; G. B. Wilson et al., 1983, In: *Immunobiology of Transfer Factor* (Kirkpatrick, C. H., Lawrence, H. S. and Burger, D. R., eds.) Academic Press, pp 331–346; Ibid, p. 213].

B. Preparation of Colostral Cell-Associated Transfer Factor Specific for *M. bovis*

Colostral leukocyte cells obtained by the method of Example 1A were disrupted by using freeze-thaw lysis. The leukocyte lysate was then dialyzed against pyrogen-free, sterile water and the dialysate (containing DLE) lyophilized. The lyophilized material was then reconstituted in water and extracted with phenol and ether. The extracted aqueous phase, which contained the cell-associated TF, was then subjected to step-wise fractional precipitation with ethanol using 0.5, 1.0, 2.0 and 4.0 volumes of ethanol. The TF-containing fraction was then further purified by cellulose tlc.

C. Procedures for Testing for TF Activity

Colostral whey or products obtained from fractionating the colostral whey were tested for TF activity using both in vivo and in vitro TF assays. DLE prepared from colostral cells or fractions obtained therefrom was tested in vitro. TF has been defined classically as a substance derived from immune cells which can transfer antigen specific delayed-type hypersensitivity in vivo (Wilson, G. B. and Fudenberg, H. H., 1983, Immunology Today 4:157). To document in vivo transfer of delayed-type hypersensitivity Balb/c mice were injected intraperitoneally with various amounts of TF obtained from colostral whey of cows immune to *M. bovis*. Control Balb/c mice received either analogous material obtained from cows not immune to *M. bovis* or saline. Twenty-four hours later transfer of reactivity to *M. bovis* was determined by the foot pad swelling test which is a standard assay for measurement of delayed type hypersensitivity in mice (Gray, D. F. and Jennings, P. A., 1955, Amer. Rev. Tuberc. Pulmonary Dis. 72:171; Van Dijk, H., Versteeg, H. and Hennink, H. J., 1976, J. Immunol. Methods 12:261). TF activity was documented in vitro by using a newly developed assay, the leukocyte migration inhibition (LMI) test employing as target cells peripheral blood leukocytes from human donors nonresponsive for *M. bovis* (Wilson, G. B. and Fudenberg, H. H., 1981, Lymphokines 4:107).

D. Test Results Obtained Using the Foregoing Procedures: Transfer of Immune Reactivity in vitro and in vivo (i) TFe in or Derived from Colostral Whey Table II shows the results of injecting Balb/c mice with colostral whey or fractions obtained from colostral whey after phenol and ether extraction, ethanol precipitation and cellulose thin-layer chromotography. Only colostral whey or fractions obtained from colostral whey derived from cows immune to *M. bovis* were active in transferring significant delayed-type hypersensitivity to mice. In addition, the TF obtained after sequential fractionation of colostral whey (using phenol-ether extraction, then ethanol precipitation and then cellulose TLC) was of a potency equal to or greater than the TF harbored in crude whey. It is noteworthy that no TF activity could be detected by either in vivo or in vitro assay (see below) in the material retained in the bag after dialysis of the whey; only the dialysate (material which came through the bag) contained TF activity.

TABLE II

Transfer of Delayed-Type Hypersensitivity to *M. bovis* in Balb/c Mice as Shown by the Footpad Test

| Substance injected | Footpad response[a] |
|---|---|
| 1. (a) Colostral whey from cows immune to *M. bovis* | 30.00[b] |
| (b) Colostral whey from cows not immune to *M. bovis* | 8.00 |
| (c) Saline control | 3.00 |
| 2. (a) TF contained in dialysate from 1a | 32.00[b] |
| (b) Analogous material contained in dialysate from 1b | 7.00 |
| (c) Saline control | 3.00 |
| 3. (a) TF containing fraction obtained from 2a after phenol and ether extraction | 50.00[b] |
| (b) Analogous fraction obtained from 2b after phenol and ether extraction | 5.00 |
| (c) Saline control | 3.00 |
| 4. (a) TF containing fraction obtained from 3a after ethanol precipitation and cellulose thin-layer chromatography | 42.00[b] |
| (b) Analogous fraction obtained from 3b after ethanol precipitation and cellulose thin-layer chromatography | 4.00 |
| (c) Saline control | 3.00 |

[a] Mean increase in footpad thickness in 0.01 mm 24 hr after injection of 10 μg of PPD-B.
[b] Significant increase (P < 0.01).

The leukocyte migration inhibition (LMI) assay has been shown to be a reproducible sensitive assay for use in detecting TF in vitro (Wilson and Fudenberg, 1981).

Table III shows typical results for testing fractions of colostrum and colostral whey for TF activity for PPD-B using the LMI assay. The test results in this and subsequent tables were obtained with material either at the original concentration e.g. colostral whey; or if further puprified, e.g. by dialyis then from material reconstituted to a volume equivalent (i.e. 1x concentration) to the material in previous steps from which it was derived. Only colostral whey from cows immune to *M. bovis* was active in inducing responsiveness to PPD-B in human lymphocytes previously nonresponsive to PPD-B. No TF activity was found associated with the fat removed from crude colostrum by centrifugation nor was colostral whey from cows nonimmune to *M. bovis* able to induce cellular immune responsiveness to PPD-B in vitro (e.g., it did not contain TF specific for PPD-B). Evaluations for TF activity of the material retained in the dialysis bag and of the material which was found in the dialysate (MW<20,000) after colostral whey was dialysed against water, indicated unequivocally that all of the material capable of inducing cellular immune responsiveness to PPD-B was in the dialysate (Table III). These results are consistent with our contention that TF is present in colostral whey since it is of MW<20,000 (Wilson and Fudenberg, 1981).

TABLE III

Documentation of Transfer Factor Activity for PPD-B in Colostral Whey and Dialyzable Colostral Whey

| Material tested | Amount (μl) tested | LMI activity (% $D_B$)[a] |
|---|---|---|
| Fat obtained from colostrum of cows immune to PPD-B | 30 | 0.0 |
| Colostral whey obtained from cows immune to PPD-B | 30 | +32.0 |
| Colostral whey obtained from cows nonresponsive to PPD-B | 30 | −10.0 |
| Material retained in dialysis bag after dialysis of colostral whey from cows immune to PPD-B | 40 | −5.0 |
| Dialysate from colostral whey of cows immune to PPD-B | 16 | +21.0 |

[a] % $D_B = (1 - MI_B/MI_A) \times 100$. % $D_B$ values greater than +15 are significant (P < .01) and indicate that antigen specific responsiveness was induced by TF present in the material tested. $MI_B$ = migration index derived from comparing cells incubated with test material plus antigen in medium versus antigen only in medium. $MI_A$ = migration index derived from comparing cells incubated with test material in medium versus medium alone.

(ii) Cell-Associated TF

Table IV shows the results for testing cell-derived fractions obtained in Example 1B, above, for TF activity usig the LMI assay. TF activity was oserved in the phenol and ether-extracted, ethanol-precipitated material. TLC was found to improve the purity of the TF.

TABLE IV

Documentation of Transfer Factor Activity for Fractions Obtained from Colostral Leukocyte Lysate

| Material tested | Amount (μl) tested | LMI activity (% $D_B$)[a] |
|---|---|---|
| Leukocyte dialysate after phenol and ether extraction and EtOH precipitation | 20 | +21 |
| Material further purified with TLC | 40 | +23 |

[a] % $D_B$ as defined below Table III. The human cells were not responsive to M. bovis (100 μg/ml) alone, i.e., in the absence of the material tested.

E. Further Results

To futher document that colostrum from cows immune to PPD-B harbors TF specific for PPD-B the ability of their dialyzable colostrum to unduce cellular immune responsiveness to M. fortuitum (PPD-F), M. mariamum (PPD-M) and M. intracellulare (PPD-I) was tested. The cows were not known to have immunity to (PPD-I) F, or M.

As the results in Table V illustrate, colostrum from cows immune to M. bovis induced immunity only to PPD-B, not to PPD-I, F or M. Thus, only transfer factor specific to the organism used for immunizing the cows was produced; this documents the selectivity one can achieve.

TABLE V

Specificity of TF in Dialyzable Fraction of Colostral Whey

| Antigen tested (100 μg/ml) | LMI activity $MI_A/MI_B$[a] | (% $D_B$) |
|---|---|---|
| PPD-B | 0.94/0.79 | (+16) |
| PPD-M | 0.94/0.92 | (+2) |
| PPD-F | 0.94/0.95 | (−1) |
| PPD-I | 0.94/0.99 | (−5) |

[a]Activity for 16 μl of the dialyzable fraction of colostral whey from cows immune to PPD-B. % $D_B$ values greater than +15 are significant.

EXAMPLE 2

Colostral Excreted TF Specific for Various Additional Antigens

A. Preparation of Colostral TFe (i) TFe Specific for *Coccidioides immitis*

Pre- or post parturition colostrum samples were obtained from dairy cows previously immunized with spherulin, a formalin-fixed spherule form of *C. immitis,* a fungal organism which produces disease in humans. Control dairy cows were used in this study to substantiate the requirement of immunization of a dairy cow to obtain TFe's of the desired specificity in post parturition colostrum The crude colostrum samples were centrifuged at 3,000–12,000 g at 4° C. for 15 min. to pellet the cells. The fat was skimmed from the supernatant and the remaining supernatant was decanted. An equal volume of cold (ca. 4° C.) acetone was then added to the decanted supernatant with mixing. The mixture so produced was centrifuged at 12,000 g for 10 min. at 4° C. to pellet casein, immunoglobulins, other proteins and contaminants. The supernatant was then concentrated with a rotary evaporator to remove acetone and reduce the volume. The material so obtained was sterilized with a Nalgene 0.2μ sterile filter unit. The aqueous concentrate was lyophilized to yield a dry residue containing TFe.

(ii) TFe specific for Herpes simplex virus (HSV)

Example 2-A(i) was repeated using dairy cows immunized with live HSV-1 instead of *C. immitis.* A dry residue was again obtained.

(iii) TFe specific for Marek's disease (MD) virus

Example 2-A(i) was repeated using dairy cows immunized with a commercially available chicken vaccine containing live Marek's disease virus instead of *C. immitis.* A dry residue was again obtained.

(iv) TFe specific for Newcastle's disease (ND) virus

Example 2-A(i) was repeated using dairy cows immunized with a commercially available chicken vaccine containing live Newcastle's disease virus instead of *C. immitis.* A dry residue was again obtained.

(v) TFe specific for Infectious bronchitis (IB) virus

Example 2-A(i) was repeated using dairy cows immunized with a commercially available chicken vaccine containing live infectious bronchitis virus instead of *C. immitis.* A dry residue was again obtained.

(vi) TFe specific for laryngotracheitis (LT) virus

Example 2-A(i) was repeated using dairy cows immunized with a commercially available chicken vaccine containing live laryngotracheitis virus instead of *C immitis.* A a dry residue was again obtained.

(vii) TFe specific for bovine rhinotracheitis (BRT) virus

Example 2-A(i) was repeated using dairy cows immunized with a commercially available bovine vaccine containing live BRT virus instead of *C. immitis*. A dry residue was again obtained.

(viii) Preparation of material with a cream separator

Examples 2-A(i)-(vii) were repeated using a cream separator instead of a centrifuge for the removal of fat and cells. Results obtained using the cream separator were similar to those obtained using the centrifuge.

(ix) Preparation of material from milk

Examples 2-A(i)-(viii) were repeated using milk instead of colostrum. Similar results were obtained (x) Preparation using high speed centrifugation Examples 2-A(i)-(viii) were repeated and the decanted supernatant was subjected to high speed centrifugation (18,00 g) at 4° C. for 30 min. to remove additional material (e.g., casein) before the precipitation step.

(xi) Nine-volume precipitation

Examples 2-A(i)-(viii) were repeated using 8 additional volumes of acetone to effect precipitation of TFe from the supernatant of the 1-volume precipitation procedure, i.e. at an acetone:aqueous volume ratio of 9:1. The mixture was centrifuged a 12,000 g for 10 min at 4° C. The 9-volume precipitation essentially replaces the rotary evaporation and lyophilization in the procedure of Example 1-A(i).

B. Procedures for Testing TF Activity (i) in vitro

The residues obtained in Examples 2-A(i)-(xi) were tested for activity using the LMI assay of Example 1-C employing as target cells peripheral blood leukocytes from human donors non-responsive to Spherulin, HSV-1, MD virus, ND virus, IB virus, LT virus or BRT virus.

(ii) in vivo

The residues were also tested for in vivo activity in specific pathogen-free (SPAFA) 1-day to 30-day old white leghorn chickens or in unvaccinated commercial white leghorn cockerels by administering various amounts of each product (10–4,000 μl) to the chicken either orally or by intramuscular injection. Two to 30 days after administration the chickens were evaluated to determine if specific cell mediated immunity to the respective antigen had been induced. The evaluation was conducted using an agarose LMI assay (adapted from K. V. Nagaraja, J. A. Newman and B. S. Pomeny, Am. J. Vet. Res., 1982, 43:916-918). Leukocytes were obtained by cardiac puncture and the cells were incubated with the various vaccines (heat inactivated, 56° C., 15 min) before being dispensed into wells punched in the agarose plates. Leukocytes were also obtained from 15 to 30 week old white leghorn chickens which had previously been vaccinated with MD, ND, IB or LT vaccines and from SPAFA and white leghorn cockerels which were unvaccinated with respect to the specific pathogen and did not receive any of the materials being tested.

C. Test Results Obtained Using the Foregoing Procedures (i) in vitro LMI assay using human target cells Table VI summarizes results obtained by testing colostral residues obtained in Example 2-A(i)-(vii) for TF activity for the various pathogens. Testing was conducted using the LMI assay with human target cells. Table VII shows results indicating that TF (specific for BRT or spherulin) remaining in the supernatant after a 1-volume acetone precipitation may be recovered in a 9-volume acetone precipitation.

(ii) in vivo testing: transfer of cell mediated immunity to chickens

Table VIII summarizes the range of MI (migration inhibition) values obtained for vaccinated control chickens and non-immune chickens to LT, ND, MD or IB in LMI assays. Prior to receiving preparations containing TF, neither SPAFA chickens or unvaccinated commercial white leghorn chickens (commercial non-immune chickens) responded to any of the four (4) viruses or to BRT. SPAFA and commercial non-immune chickens both showed similar response to each of the four (4) viruses after receiving TF preparations, thus the results shown below are not related to the type of chicken tested.

TABLE VI

Documentation of Transfer Factor Activity for Colostral Fractions Obtained by Acetone Precipitation Using LMI Assay

| Material Tested | Amount[a] Tested (μl) | Antigen[b] | LMI Activity[c] (% $D_B$) |
|---|---|---|---|
| Reconstituted lyophilized supernatant of 1 volume acetone precipitation | 20 | BRT | +22 |
| | 20 | Spherulin | +21 |
| | 20 | HSV-1 | +24 |
| | 40 | LT | +23 |
| | 30 | ND | +33 |
| | 30 | MD | +28 |
| | 40 | IB | +30 |

[a]Material obtained in Example 2-A(i)-(ix) was reconstituted in a pyrogen-free water (2x), filtered and then tested in the LMI assay using human target cells.
[b]BRT, Spherulin, HSV-1, LT, ND, MD and IB are as defined previously.
[c]% $D_B$ as defined in Table III.

TABLE VII

Recovery of TF Activity in 1-volume Acetone Precipitation Supernatant by 9-Volume Acetone Precipitation

| Material Tested | Amount[a] (μl) | Antigen[b] | LMI Activity[c] (% $D_B$) |
|---|---|---|---|
| Reconstituted supernatant of 1-volume acetone precipitation | 20 | BRT | +22 |
| | 20 | Spherulin | +21 |
| Reconstituted 9-volume acetone precipitate from 1-volume acetone supernatant | 20 | BRT | +20 |
| | 20 | Spherulin | +29 |

[a] [b] [c]As in Table VI and text.

The effects of TF preparations were dose dependent (tested over a range of 10 μl to 4,000 μl/bird), however, the effects noted were independent of the route of administration (oral/intramuscular).

The ability of fractions ottained from reconstituted supernatants of 1-volume acetone precipitations from colostral whey to induce immunity to LT, ND, MD or IB viruses in previously non-immune chickens is illustrated by the results shown in Table IX. In each case the effects of fractions obtained from cows immunized with the respective poultry vaccine iscompared to analogous fractions from cows not immunized with the respective poultry vaccine, and immune only to BRT virus.

It is of interest to note that chickens which received fractions prepared from cows immunized with the four poultry vaccines became responsive to LT, ND, IB, MD and BRT whereas fractions prepared from cows not immunized by the four poultry vaccines induced immunity in chickens to only BRT. Reconstituted nine-volume acetone precipitates of active supernatants from one-volume acetone precipitated samples readily induce immunity in chickens as shown by the data presented in Table X.

TABLE VIII

Summary of Cell Mediated Immune Responsiveness: Responsiveness of Vaccinated Immune Chickens and Non-Immune Chickens to LT, ND, MD or IB Viruses as Shown By LMI Assay

| Anti-gen | MI Cut-off for No response | MI Values[a] Non-immune | (N)[b] | Immune | (N)[c] |
|---|---|---|---|---|---|
| LT | 0.85 | 0.85–1.03 | (23) | 0.59–0.77 | (8) |
| ND | 0.90 | 0.91–1.17 | (18) | 0.45–0.88 | (8) |
| MD | 0.90 | 0.90–1.07 | (17) | 0.56–0.79 | (7) |
| IB | 0.90 | 0.98–1.18 | (17) | 0.59–0.85 | (9) |

[a]MI = migration index.
[b]N non-immune = number of groups of birds tested.
[c]N immune = number of individual birds.

TABLE IX

Effect of Fractions Obtained by Acetone Precipitation of Colostrum on Immunity in Chickens

| Preparation Birds Received | Amount (μl) | Antigen | Response MI[a] |
|---|---|---|---|
| Reconstituted supernatant of 1-volume acetone precipitation from colostrum of cows immunized with poultry vaccines | 500 | LT<br>ND<br>IB<br>MD<br>BRT | 0.71<br>0.69<br>0.67<br>0.73<br>0.76 |
| Reconstituted supernatant of 1-volume acetone precipitation from colostrum of cows not immunized with poultry vaccines (immune to BRT virus only) | 500 | LT<br>ND<br>IB<br>MD<br>BRT | 0.96<br>0.98<br>1.08<br>1.00<br>0.65 |

[a]Results are mean values for four or more experiments involving separate groups of birds.

TABLE X

Effects of Reconstituted 9-Volume Acetone Precipitated Material from Colostrum on Induction of Immunity in Chickens

| Preparation[a] Birds Received | Amount (μl) | Antigens | Response MI[b] |
|---|---|---|---|
| 1. 587–823 | 500 | ND; IB | 0.74; 0.75 |
| 2. 587–827 | 500 | ND; IB | 0.69; 0.69 |
| 3. 189–67 | 500 | ND; MD | 0.79; 0.67 |
| 4. 224–911 | 500 | ND; MD | 0.64; 0.50 |

[a]Reconstituted 9-volume acetone precipitation from colostral samples from cows immunized with all four poultry vaccines. Numbers refer to sample numbers.
[b]MI values are mean values from three or more experiments using different groups of birds.

EXAMPLE 3

Colostral Excreted Transfer Factor (TFe) Specific for Various Antigens Including Newcastle's Disease Virus A. Preparation of TFe (i) *C. immitis*

Colostrum was obtained from a cow immunized with Spherulin and the fat and cells removed as in Example 2-A(i). The low fat product was dialyzed twice against four volumes of cold sterile distilled water using dialysis membranes of 12,000 M.W. cut-off. The TF-containing dialysates (i.e. the material which passed through the membrane) were collected, combined and concentrated via lyophilization.

(ii) laryngotracheitis (LT) virus

Example 3-A was repeated with colostrum obtained from a cow immunized with LT virus as in Example 2-A(vi).

(iii) Newcastle's Disease (ND) virus

Example 3-A was repeated with colostrum obtained from a cow immunized with ND virus as in Example 2-A(iv).

(iv) Infectious bronchitis (IB) virus

Example 3-A was repeated with colostrum obtained from a cow immunized with IB virus as in Example 2-A(v).

(v) Marek's Disease (MD) virus

Example 3-A was repeated with colostrum obtained from a cow immunized with MD virus as in Example 2-A(iii).

B. Procedures for Testing for TF Activity

The TF activity of the lyophilized residues obtained in Examples 3-A was assayed by the procedures of Example 2.

C. Results Obtained Using the Foregoing Procedures (i) in vitro

The material obtained in Example 3-A(i) induced a responsiveness for Spherulin in previously non-responsive human cells in the LMI assay (MI values greater than 0.90 when cells were incubated with spherulin in medium).

(ii) in vivo

The material obtained in Example 3-A(iii) was capable of inducing in chickens antigen-specific cell mediated immunity to Newcastle's disease, as shown in Table XI. Table XI also presents data for material obtained by the method of Example 3-A(iii) which was further purified by various methods described in the preceding examples.

TABLE XI

Induction of Immunity to ND Virus in Chickens by Injection of Fractions from Colostrum Obtained by Dialysis, Phenol-Ether Extraction and Acetone Precipitation

| Preparation Chickens Received | Amount given (μl) | Response to ND Virus (MI)[a] |
|---|---|---|
| 1. Reconstituted dialysate of colostrum | 250 | 0.67 |
| 2. Reconstituted water phase obtained after phenol-ether extraction of #1 | 250 | 0.67 |
| 3. Reconstituted supernatant of 1-volume acetone precipitation of #1 | 250 | 0.74 |
| 4. Reconstituted 9-volume acetone precipitation of supernatant from #3 | 250 | 0.62 |

[a]Results and mean MI values for experiments involving 3 or more separate groups of non-immune birds who received the preparations shown.

EXAMPLE 4

Colostral Excreted Transfer Factor (TFe) specific for *Coccidioides immitis* Obtained by Isopropanol Precipitation A. Preparation of TFe Colostrum was obtained and fat and cells removed by the method of Example 2-A(i). The low fat product was mixed with an equal volume of cold isopropanol. The mixture was centrifuged at 12,000 g for 10 min. at 4° C. to pellet contaminants. Additional cold isopropanol was mixed with the supernatant to achieve a final ratio of two parts isopropanol to one part aqueous liquid. The material was then centrifuged at 12,000 g for 10 min. at 4° C. and the pellet collected. The supernatant was then treated with additional isopropanol (up to a ratio of 5 parts isopropanol to 1 part aqueous liquid). By centrifuging again, additional TF in the pelleted material was recovered.

B. Procedure for Testing for TFe Activity

Material obtained in Example 4-A was tested for TF activity by the LMI assay method of Example 1.

C. Test Results Obtained by the Foregoing Procedure

Results obtained using the LMI assay are shown in Table XII and document the induction of immunity by TFe in otherwise non-responsive human cells. It is clear from the results shown in Table XII that by adjusting the volume of added isopropanol the yield of TF can be mximized.

TABLE XII

Induction of Immunity to Spherulin by Excreted TF in Colostral Fractions Obtained by Isopropanol Precipitation

| Material Tested | Amount (μl) | Response[a] (% $D_B$) |
|---|---|---|
| Reconstituted precipitate obtained by using 2.0 volumes of Isopropanol | 40 | +37 |
| Reconstituted precipitate obtained by using 5.0 volumes of Isopropanol | 50 | +26 |

[a]Response to Spherulin in human target cells as shown by leukocyte migration inhibition. All target cells were non-responsive to Spherulin without addition of the materials tested. % $D_B$ as in Table III.

EXAMPLE 5

Colostral Excreted Transfer Factor (TFe) Specific for Human Mumps Virus

A. Preparation

Colostral whey was prepared by the method of Example 1 by recovering colostrum from a cow immunized with bovine parainfluenza virus using low speed centrifugation followed by high speed centrifugation.

B. Procedure for Testing for TF activity

The activity of the TF so obtained was assayed by the in vitro LMI assay described in Example 1.

C. Test Results Obtained by the Foregoing Procedure

Assay results for TF specific for human mumps virus are show in Table XIII and document the induction by TFe of immunity in otherwise non-responsive human cells. Additionally, the material obtained and tested in this example may be fractionated or further purified and then sterilized by the methods previously described. The sterile, higher potency product thereby obtained may be administered to a human subject with mumps in order to alleviate or cure the disease. Furthermore, the TF-containing product may be administered to a human subject not infected with mumps virus so as to confer immunity to the disease. The results indicate some cross reactivity in the cellular immune response to human mumps virus and bovine parainfluenza virus which are both paramyxoviruses.

TABLE XIII

Induction of Immunity in Human Cells to Mumps Virus or Bovine Parainfluenza-3 Virus by Colostral Whey as Shown By Leukocyte Migration Inhibition Assay

| Material[a] Tested | Amount (μl) | Antigen | Response[b] (% $D_B$) |
|---|---|---|---|
| Colostral whey preparation 716-2 | 15 | Mumps virus | +20 |
| Colostral whey preparation 754-1 | 30 | Parainfluenza virus | +35 |

[a]Colostral whey was prepared by first low speed centrifugation followed by high speed centrifugation to remove cells, debris, fat and casein.
[b]Response to each antigen as shown by leukocyte migration inhibition using human target cells not responsive to either antigen alone (without the material tested present). % $D_B$ as defined in Table III.

EXAMPLE 6

Colostral Excreted Transfer Factor Specific for bovine parainfluenza-3 virus

A. Preparation

Colostral whey was prepared by the method of Example 1 by recovering colostrum from a cow immunized with bovine parainfluenza-3 virus using low speed centrifugation followed by high speed centrifugation.

B. Procedure for Testing for TF activity

The activity of the TF so obtained was assayed by the in vitro LMI assay described in Example 1.

C. Test Results Obtained by the Foregoing Procedure

Assay results for TF specific for bovine parainfluenza-3 virus are shown in Table XIII and document the induction of immunity by TFe in otherwise non responsive human cells.

What is claimed is:

1. A method of obtaining a cell-free fluid containing excreted transfer factor (TFe) specific for an antigen which comprises collecting material secreted by the mammary gland of a suitable lactating mammal, treating the material to separate cells, cell debris, casein, fat and ther substances which interface with transfer factor efficacy so as to produce a cell-free fluid containing the excreted transfer factor, dicarding the separated cells, cell debris, casein, fat and other substances, and recovering the cell-free fluid containing the excreted transfer factor.

2. A method according to claim 1, wherein the material is colostrum.

3. A method according to claim 1, wherein the material is milk.

4. A method according to claim 1, wherein the suitable lactating mammal is a cow which has immunity to the antigen.

5. A method according to claim 4, wherein the cow is rendered immune by injecting the antigen or transfer factor specific for the antigen or exposing the cow to the antigen before the cow commences lactation.

6. A method according to claim 1, wherein the treating comprises ultrafiltration.

7. A method according to claim 1, wherein the treating comprises dialysis.

8. A method according to claim 1, wherein the treating comprises low speed centrifugation for a period of time, followed by high speed centrifugation for another period of time.

9. A method according to claim 1, wherein the treating comprises low speed centrifugation for a period of time, followed by addition of a suitable amount of an agent which substantially precipitates immunoglobulins.

10. A method according to claim 1, wherein the treating comprises low speed centrifugation for a period of time, followed by ultrafiltration.

11. A method according to claim 1, wherein the treating comprises low speed centrifugation for a period of time, followed by dialysis.

12. A method according to claim 1, which further comprises concentration or purifying the cell-free fluid containing the excreted transfer factor so as to obtain concentrated or purified transfer factor.

13. A method according to claim 1, wherein the antigen is a microorganism or is derived therefrom.

14. A method according to claim 13, wherein the antigen is a bacterium or is derived therefrom.

15. A method of claim 14, wherein the bacterium is *Mycobacterium bovis*.

16. A method according to claim 13, wherein the antigen is a fungus or is derived therefrom.

17. A method of claim 16, wherein the fungus is *Coccidioides immitis*.

18. A method according to claim 13, wherein the antigen is a protozoan or is derived therefrom.

19. A method according to claim 1, wherein the antigen is a virus or is derived therefrom.

20. A method of claim 19, wherein the virus is herpes simplex virus.

21. A method of claim 19, wherein the virus is human mumps virus.

22. A method of claim 19, wherein the virus is bovine rhinotracheitis.

23. A method of claim 19, wherein the virus is bovine parainfluenza virus.

24. A method of claim 19, wherein the virus is Newcastle disease virus.

25. A method of claim 19, wherein the virus is Marek's disease virus.

26. A method of claim 19, wherein the virus comprises infectious bronchitis virus.

27. A method of claim 19, wherein the virus comprises laryngotracheitis virus.

28. A method according to claim 1, wherein the antigen is cancer-related.

* * * * *

UNITED STATES PATENT AND TRADEMARK OFFICE
CERTIFICATE OF CORRECTION

PATENT NO. : 4,816,563

DATED : March 28, 1989

INVENTOR(S) : Gregory B. Wilson; Gary V. Paddock

It is certified that error appears in the above-identified patent and that said Letters Patent is hereby corrected as shown below:

Column 1, line 38, change "Colostral Cytotoxicity" to
--colostral cytotoxicity--.
Column 2, line 23, change "effrrt" to --effort--.
Column 3, line 26, change "te" to --the--;
line 40, change "fr.om" to --from--.
Column 4, line 4, delete "parturition";
line 37, after "of" insert --C. immitus--;
line 52, after "abandoned" insert --,--;
line 53, after "1983" insert --in the--.
Column 5, line 28, change "38" to --380--.
Column 6, line 38, after "to" insert --remove--.
Column 7, line 12, change "Immunobioloov" to -- Immunobiology--;
line 46, change "micoplasma" to --mycoplasma--.
Column 8, line 67, change "atural" to --natural--.
Column 9, line 49, after "By" insert --this--.
Column 10, line 27, change "." to --,--.
Column 12, line 38, change "immunogen" to --immunogens--.
Column 14, line 58, change "puprified" to --purified--,
and change "dialyis" to --dialysis--.

UNITED STATES PATENT AND TRADEMARK OFFICE
CERTIFICATE OF CORRECTION

PATENT NO. : 4,816,563

DATED : March 28, 1989

INVENTOR(S) : Gregory B. Wilson; Gary V. Paddock

It is certified that error appears in the above-identified patent and that said Letters Patent is hereby corrected as shown below:

Column 15, line 62, change "(PPD-I)" to --PPD-I,--.
Column 17, line 14, change "18,00 g" to --18,000 g--;
          line 25, change "1-A(i)." to --2-A(i).--;
          line 26, change "activitiv" to --activity--.
Column 18, line 52, change "ottained" to --obtained--;
          line 58, change "iscompared" to --is compared--.
Column 21, line 24, change "mximized" to -maximized--;
          line 55, change "show" to --shown--.
Column 22, line 32, change "non responsive" to --non-responsive--.

IN THE CLAIMS

Column 22, line 41, change "ther" to --other--;
          line 43, change "dicarding" to --discarding--.

Signed and Sealed this

Fifth Day of June, 1990

Attest:

HARRY F. MANBECK, JR.

*Attesting Officer*     *Commissioner of Patents and Trademarks*